(12) United States Patent
Kulidjian

(10) Patent No.: US 11,129,732 B2
(45) Date of Patent: Sep. 28, 2021

(54) SYSTEMS AND METHODS FOR SELECTING ARTIFICIAL FEMORAL COMPONENTS

(71) Applicant: X40, Inc, La Jolla, CA (US)

(72) Inventor: Anna Andranik Kulidjian, La Jolla, CA (US)

(73) Assignee: X40, Inc., La Jolla, CA (US)

( * ) Notice: Subject to any disclaimer, the term of this patent is extended or adjusted under 35 U.S.C. 154(b) by 268 days.

(21) Appl. No.: 16/392,282

(22) Filed: Apr. 23, 2019

(65) Prior Publication Data

US 2020/0337865 A1   Oct. 29, 2020

(51) Int. Cl.
| | | |
|---|---|---|
| *A61B 17/00* | (2006.01) | |
| *A61F 2/46* | (2006.01) | |
| *A61B 17/15* | (2006.01) | |
| *A61F 2/38* | (2006.01) | |
| *A61B 90/00* | (2016.01) | |

(52) U.S. Cl.
CPC .......... *A61F 2/4657* (2013.01); *A61B 17/155* (2013.01); *A61F 2/3859* (2013.01); *A61F 2/461* (2013.01); *A61B 2090/0807* (2016.02); *A61F 2002/4658* (2013.01)

(58) Field of Classification Search
CPC combination set(s) only.
See application file for complete search history.

(56) References Cited

U.S. PATENT DOCUMENTS

| | | | |
|---|---|---|---|
| 4,566,466 A | 1/1986 | Ripple et al. | |
| 4,567,885 A | 2/1986 | Androphy | |
| 4,759,350 A | 7/1988 | Dunn et al. | |
| 5,306,285 A | 4/1994 | Miller et al. | |
| 5,462,549 A | 10/1995 | Glock | |
| 5,613,969 A | 3/1997 | Jenkins, Jr. | |
| 5,776,137 A | 7/1998 | Katz | |
| 6,875,222 B2 | 4/2005 | Long et al. | |
| 7,744,616 B2 | 6/2010 | O'Donoghue | |
| 7,789,885 B2 | 9/2010 | Metzger | |
| 8,323,288 B2 | 12/2012 | Zajac | |
| 8,545,506 B2 | 10/2013 | Long et al. | |
| 8,828,020 B2 | 9/2014 | Dower et al. | |
| 8,882,776 B2 | 11/2014 | Long et al. | |

(Continued)

OTHER PUBLICATIONS

International Search Report dated Aug. 11, 2020, in International Application No. PCT/US20/29565, filed Apr. 23, 2020; 3 pages.

*Primary Examiner* — Sameh R Boles
(74) *Attorney, Agent, or Firm* — Jason R. Jones

(57) ABSTRACT

A system for preparing a femur to receive an implant includes a saw blade, positionable in a saw blade slot of a distal cutting block and operable to form an axial cut surface on the patient's femur. The saw blade carries nominal sizing indicia that increments negatively from an anterior top of concavity of the medial condyle to a posterior top of concavity of the medial condyle, when the saw blade is positioned on the axial cut surface of the patient's femur. An A/P chamfer cutting block is positionable on an axial cut surface of a femur, the A/P chamfer cutting block carrying at least one rotational guide, the at least one rotational guide positionable on a posterior surface of at least one of the medial condyle or the lateral condyle of the patient's femur to thereby rotationally orient the chamfer cutting block relative to the patient's femur.

11 Claims, 4 Drawing Sheets

(56) References Cited

U.S. PATENT DOCUMENTS

| | | |
|---|---|---|
| 9,668,746 B2 | 6/2017 | Lee et al. |
| 9,848,896 B2 | 12/2017 | Emslie et al. |
| 9,974,547 B2 | 5/2018 | Lin et al. |
| 2003/0045883 A1 | 3/2003 | Chow et al. |
| 2004/0153066 A1 | 8/2004 | Coon et al. |
| 2006/0111726 A1 | 5/2006 | Felt et al. |
| 2010/0057089 A1 | 3/2010 | Axelson, Jr. |
| 2010/0063508 A1* | 3/2010 | Borja .................. A61B 17/157 606/88 |
| 2011/0130762 A1 | 6/2011 | Metzger et al. |
| 2014/0018813 A1 | 1/2014 | Mckinnon et al. |
| 2014/0088598 A1 | 3/2014 | Bonutti |
| 2014/0249534 A1 | 9/2014 | Bertram, III |
| 2016/0256178 A1 | 9/2016 | Tuttle et al. |
| 2017/0128079 A1 | 5/2017 | Brown |
| 2018/0185097 A1 | 7/2018 | Langhorn et al. |
| 2018/0228614 A1 | 8/2018 | Lang et al. |
| 2019/0216472 A1* | 7/2019 | Shah .................. A61B 17/155 |

\* cited by examiner

Table I

| Implant Size | Maximum Distance Measured Across Medial Condyle (mm) |
|---|---|
| 5 | 56 |
| 6 | 58 |
| 7 | 61 |
| 8 | 63 |
| 9 | 65 |
| 10 | 67 |

SYSTEMS AND METHODS FOR SELECTING ARTIFICIAL FEMORAL COMPONENTS

BACKGROUND OF THE INVENTION

Field of the Invention

The present technology relates generally to systems and methods for selecting and implanting artificial femoral components.

Related Art

The present invention relates generally to systems and methods such as those utilized in techniques known as Total Knee Replacement (or Total Knee Arthroplasty, "TKA"). During a TKA procedure, load-bearing parts of the knee joint are replaced with artificial prostheses.

The femoral component of the TKA procedure is a rounded implant, mimicking the natural shape of the joint. To prepare the femur for the implant, the distal end of the femur is resected into a generally flat plane. After resection, a complex mechanism has been used to measure the anteroposterior (A/P) size of the femur to determine the proper size of the femoral implant component. This conventional device is not only very cumbersome, it typically requires access to the anterior cortex of the femur located proximally further along the surface of the femur. This requires an undesirably large incision which necessarily increases the complexity and risk of the surgery. This large incision is also cosmetically unpleasant. The large incision and complex measuring structure also contribute significantly to the duration of the procedure.

SUMMARY OF THE INVENTION

In accordance with one aspect of the technology, a method of determining a size of a femoral component to be implanted in a patient is provided. The method can include positioning a distal cutting block on a distal end of a patient's femur, the distal cutting block having a first saw blade slot associated therewith. A saw blade can be positioned in the first saw blade slot and can form an axial cut surface on the distal end of the patient's femur, at least a portion of the axial cut surface extending through the medial condyle. A maximum distance of the axial cut surface across the medial condyle can be measured. A femoral component can be selected based on the maximum distance measured.

In accordance with another aspect of the invention, a system is provided for preparing a femur to receive an implant. The system can include a saw blade, positionable in a saw blade slot of a distal cutting block and operable to form an axial cut surface on the patient's femur. The saw blade can carry nominal sizing indicia that increments negatively from an anterior top of concavity of the medial condyle to a posterior top of concavity of the medial condyle, when the saw blade is positioned on the axial cut surface of the patient's femur. An A/P chamfer cutting block can be positionable on an axial cut surface of a femur. The A/P chamfer cutting block can carry at least one rotational guide, the at least one rotational guide positionable on a posterior surface of at least one of the medial condyle or the lateral condyle of the patient's femur to thereby rotationally orient the A/P chamfer cutting block relative to posterior condyles of the patient's femur.

In accordance with another aspect of the invention, a system is provided for preparing a femur to receive an implant. The system can include a distal cutting block, operable to be positioned on a distal end of the femur, the distal cutting block including a first saw blade slot associated therewith. A saw blade can be positionable in the first saw blade slot and can be operable to resect the femur to form an axial cut surface thereon. The saw blade can carry nominal sizing indicia. An A/P chamfer cutting block can include at least a second saw blade slot associated therewith. The A/P chamfer cutting block can carry at least one rotational guide, the at least one rotational guide being operable to rotationally orient the A/P chamfer cutting block relative to the femur.

BRIEF DESCRIPTION OF THE DRAWINGS

The following drawings illustrate exemplary embodiments for carrying out the invention. Like reference numerals refer to like parts in different views or embodiments of the present invention in the drawings.

DETAILED DESCRIPTION

Figure 1:
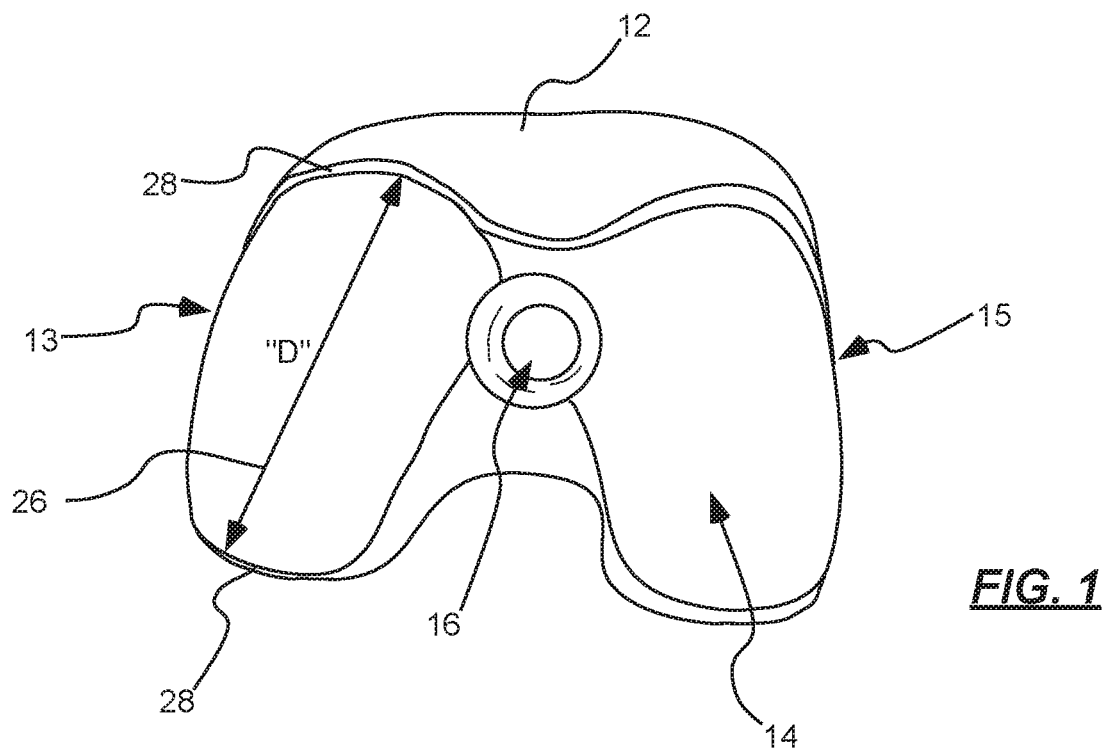
FIG. 1 is an end view of a human femur having an axial cut surface formed thereon.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Definitions

As used herein, the singular forms "a" and "the" can include plural referents unless the context clearly dictates otherwise. Thus, for example, reference to "indicia" can, if the context so dictates, include one or more signs, symbols, markings, etc.

As used herein, the term "substantially" refers to the complete or nearly complete extent or degree of an action, characteristic, property, state, structure, item, or result. As an arbitrary example, an object that is "substantially" enclosed is an article that is either completely enclosed or nearly completely enclosed. The exact allowable degree of deviation from absolute completeness may in some cases depend upon the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item so long as there is no measurable effect as a result thereof.

As used herein, the term "about" is used to provide flexibility to a numerical range endpoint by providing that a given value may be "a little above" or "a little below" the endpoint.

Relative directional terms can sometimes be used herein to describe and claim various components of the present invention. Such terms include, without limitation, "distal," "proximal," "anterior," "posterior," "upward," "downward," "horizontal," "vertical," etc. These terms are generally not intended to be limiting, but are used to most clearly describe and claim the various features of the invention. Where such terms must carry some limitation, they are intended to be limited to usage commonly known and understood by those of ordinary skill in the art in the context of this disclosure. In some instances, dimensional information is included in the figures. This information is intended to be exemplary only, and not limiting. In some cases, the drawings are not to scale and such dimensional information may not be accurately translated throughout the figures.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Invention

The present technology relates generally to techniques and apparatus for implanting femoral components as part of a partial or full knee replacement surgery. Such techniques are useful, for example, in Total Knee Replacement (or Total Knee Arthroplasty, "TKA"). During a TKA procedure, load-bearing parts of the knee joint are replaced with artificial prostheses. Typical TKA procedures can involve substantial postoperative pain and can require weeks of physical rehabilitation. The surgical incision necessary for such procedures can extend for several inches above and below the patella.

The femoral component of the TKA procedure is a rounded implant, mimicking the natural shape of the bone. To prepare the femur for the implant, the distal end of the femur is resected into a generally flat plane. After resection, a complex mechanism has conventionally been used to measure the anteroposterior (AP) size of the femur to determine the proper size of the femoral implant component. This conventional device is shown, for example, in U.S. Pat. No. 9,681,963, to Leslie et al., the disclosure of which is hereby incorporated herein by reference in its entirety. This measuring instrument is not only very cumbersome, it typically requires access to the anterior cortex of the femur located proximally further along the surface of the femur. This requires an undesirably large incision which necessarily increases the complexity and risk of the surgery. This large incision is also cosmetically unpleasant. The large incision and complex measuring structure also contribute significantly to the duration of the procedure.

The present inventor has developed techniques and instruments that significantly decrease the size of the incision required for such surgery, and also reduce the complexity of the implant component determination. The present inventor has found that her system can decrease the total surgery time by as many as twelve minutes. This decrease in surgery time is accomplished while also significantly reducing the size of incision required. Thus, the present techniques reduce costs, risks and postoperative recovery time associated with femoral implants. As the surgical incision required is also much smaller, the postoperative scarring is more cosmetically acceptable.

Implantation of femoral components is generally accomplished by creating an incision in the patient's knee to expose the ends of the femur and the tibia. Typically, a parapatellar approach is utilized, with the patella then being displaced to one side of the joint. This allows exposure of the distal end of the femur and the proximal end of the tibia. These ends are then very accurately cut and shaped to receive implant components.

While those of ordinary skill in the art will readily appreciate the surgical techniques necessary to implant femoral components, to simplify the discussion herein, the figures illustrate, sometimes partially, a human femur in isolation. This is done with the understanding that such will generally never be the case in actual practice.

Figure 2:
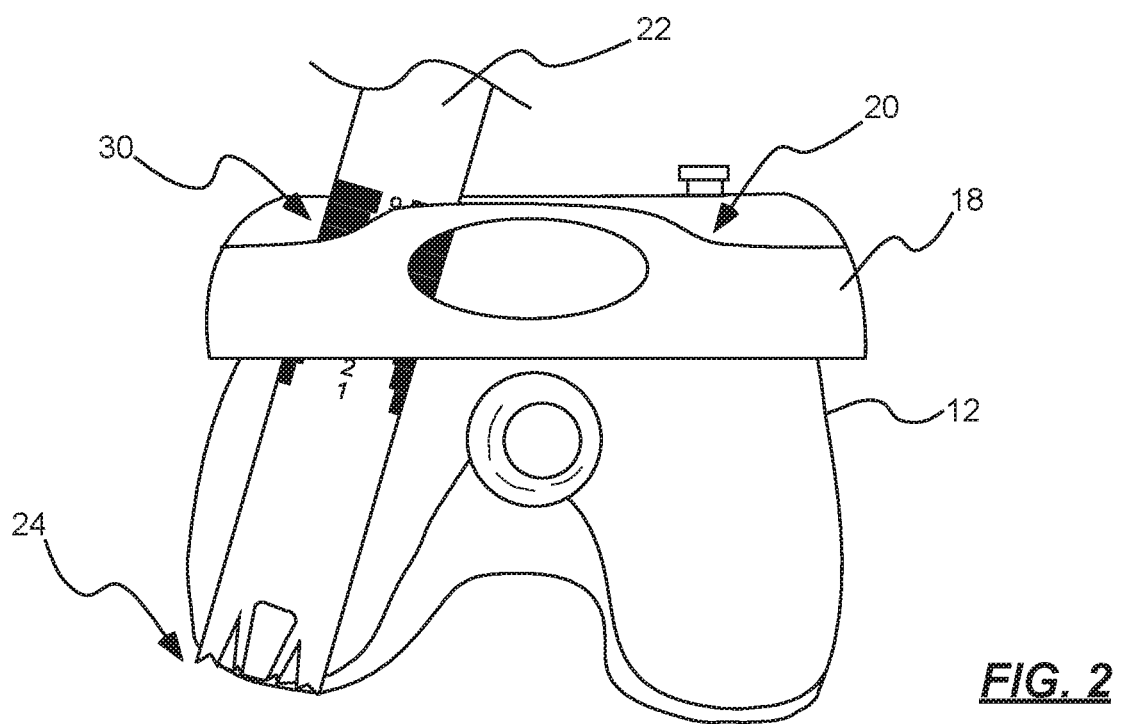
FIG. 2 is an end view of the femur of FIG. 1 with a distal cutting block positioned thereon.

Turning now to FIGS. 1 and 2, a human femur 12 is shown having had already formed thereon an axial cut surface 14. Formation of the axial cut surface can be accomplished in a number of ways. Oftentimes, an intramedullary hole or canal 16 is created in the femur to receive a rod of a resection jig (not shown). This jig can allow a distal cutting block (18 in FIG. 2) to be precisely pinned to the femur. The distal cutting block can include one or more saw blade slots 20 formed therein for receiving a saw blade 22. The saw blade shown is a sagittal saw blade with cutting teeth formed on a distal end 24. The cutting teeth and general configuration of the saw blade shown are exemplary only: a variety of differing configurations can be utilized. In addition to the sagittal blade shown, a variety of other suitable blades can be used, such as reciprocating saw blades and the like. Other techniques for removing or shaping bone can also be used, such as laser or ultrasonic saws.

The saw blade 22 is shown fully extended through the femur in FIG. 2, after the saw blade has formed the axial cut surface 14 on the femur. Generally, the saw blade is extended through the saw blade slot 20 and is coupled to a saw (on a proximal end, not shown, opposite that of end 24) that drives the saw blade in an oscillatory motion. As the saw blade is advanced through the saw blade slot, it removes bone and creates the axial cut surface shown. Generally speaking, after the axial cut surface is formed, the distal cutting block 18 can be removed.

Figure 6:
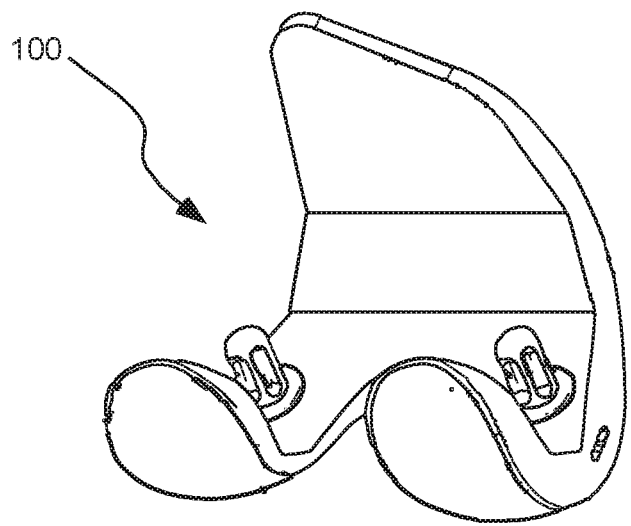
FIG. 6 is a perspective view of an exemplary PRIOR ART femoral implant component.

Once the axial cut surface 14 is formed on the distal end of the femur 12, the present system provides a manner by which a femoral implant component can be selected. An exemplary femoral implant similar to those found in the prior art is shown by example at 100 in FIG. 6. As the various sizes of such implant components vary between patients, selecting the proper size for any particular patient has been challenging and has to date required very sophisticated equipment and time-consuming techniques.

The present inventor, however, has developed a system by which the proper implant component can be relatively easily selected. As shown in FIG. 1, at least a portion of the axial cut surface 14 has been formed to extend through the medial condyle 13 (the lateral condyle is shown on the right at 15). A maximum distance 26, shown by example at dimension "D" can be measured across the medial condyle. Based, in some embodiments, solely upon this measurement, the proper size of femoral component can be selected for the particular femur.

In the example shown, the maximum distance "D" is shown extending from one surface of the bone to another surface of the bone. Generally speaking, after resection of the femur (e.g., after formation of the axial cut surface across the femur), cartilage 28 may remain on the femur around the axial cut surface. Depending upon the implant component system utilized, and the manner in which the distance is measured, the maximum distance may be measured from anterior bone surface to posterior bone surface, as shown, or may be measured from outer surface to outer surface of the cartilage 28. The measurement can also be made from bone surface to cartilage surface or cartilage surface to bone surface, etc.

Figures 3, 4:
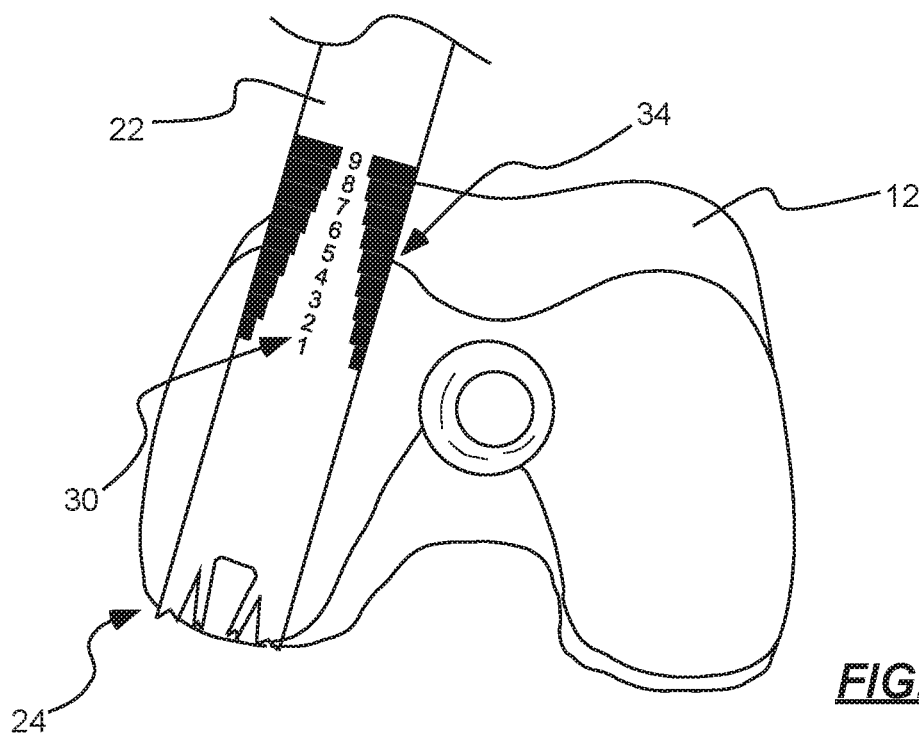
FIG. 3 is an end view of the femur of FIG. 1 with a saw blade carrying nominal sizing indicia positioned thereon.
FIG. 4 is a table showing correlating data relevant to exemplary nominal sizing indicia.
Figure 7A:
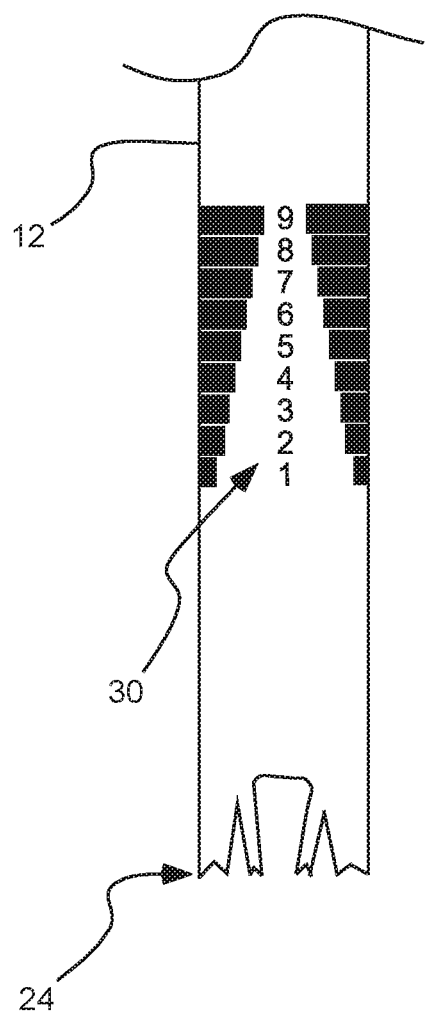
FIG. 7A is a front view of a saw blade carrying nominal sizing indicia on a front face thereof.
Figure 7B:
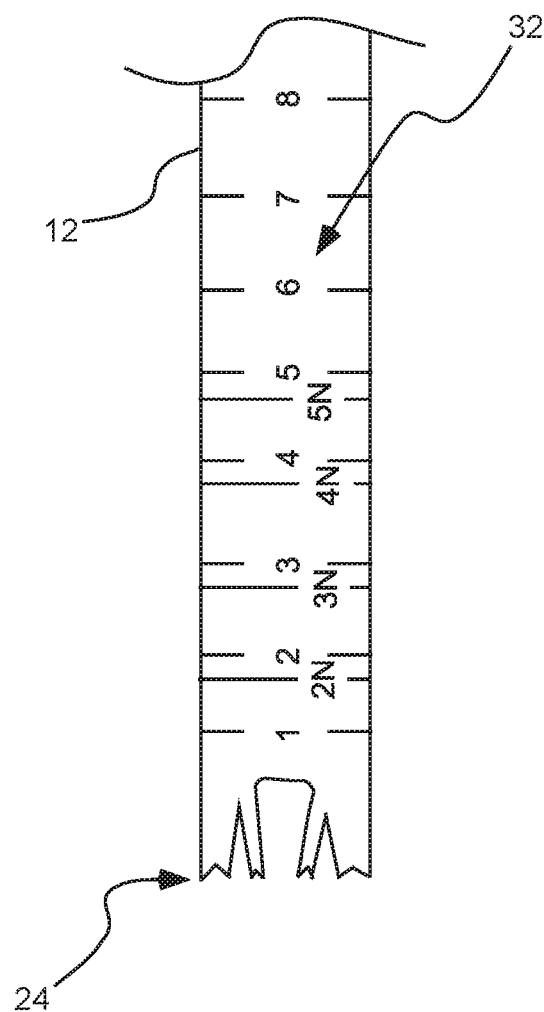
FIG. 7B is a rear view of the saw blade of FIG. 6A, showing physical dimensional indicia carried on a rear side thereof.

In one aspect of the invention, the maximum distance "D" can be measured by reviewing an image taken of the axial cut surface 14. Suitable imaging techniques can include, without limitation, CT, MRI, radiographic and other imaging modalities. The type of imaging technique utilized may also dictate which surfaces are used to measure the distance, as some imaging techniques do not capture the cartilage 28. In another aspect, the maximum distance can be measured by using indicia carried by the saw blade 22. This aspect of the invention is shown in more detail in FIGS. 3, 7A and 7B. As shown in FIG. 3, in one aspect of the technology, the maximum distance is measured using nominal sizing indicia 30 carried by the saw blade 22. The nominal sizing indicia 30 can omit any actual physical dimensional data and can be correlated to nominal sizes of femoral components. In the example shown, the nominal sizing indicia indicates that that a size 5 implant is required for the size of the femur 12 shown, as shown at reference numeral 34.

Generally speaking, the nominal sizing indicia 30 can be correlated to a particular manufacturer's implant system before applying the indicia to the saw blade 22. In this manner, a specific saw blade, having nominal sizing indicia specific to any given manufacturer, can be used for each of a number of implant component systems. Table I provides an exemplary data chart that can be used, for example, to correlate the nominal sizing to an actual dimension across the axial cut surface. This table is provided for its exemplary teaching only: the nominal sizing indicia will generally have to be tailored to each specific manufacturer.

In the examples shown, the nominal sizing indicia 30 carried by the saw blade 12 increments negatively from an anterior top of concavity of the medial condyle to a posterior top of concavity of the medial condyle, when the saw blade is positioned on the axial cut surface of the patient's femur. In this manner, the surgeon or technician can align the distal end of the saw blade with the posterior top of concavity of the medial condyle, as shown in FIG. 3, and read the correct nominal size from the indicia at the anterior top of concavity.

As shown in FIGS. 6A and 6B, in one aspect of the invention, the nominal sizing indicia 30 can be carried on a first side of the saw blade (FIG. 6A) and physical dimensional indicia 32 can be carried by a second side of the saw blade (FIG. 6B).

The physical dimensional indicia 32 can correlate to a physical size of a width of the femoral components. This indicia carried by the blade may be helpful when a surgeon or technician wishes to compare the width of the component size indicated by the sizing saw as compared to an individual patient's anatomy. To do so, a surgeon can simply place the saw on the axial cut surface and roughly visualize the femoral component called for by the A/P measurement (e.g., the reading indicated by the nominal sizing indicia) and ensure that the actual width of the implant correlates well with the patient's anatomy. This can greatly aid a surgeon in quickly deciding which implant size is best for any particular patient.

Figure 5:
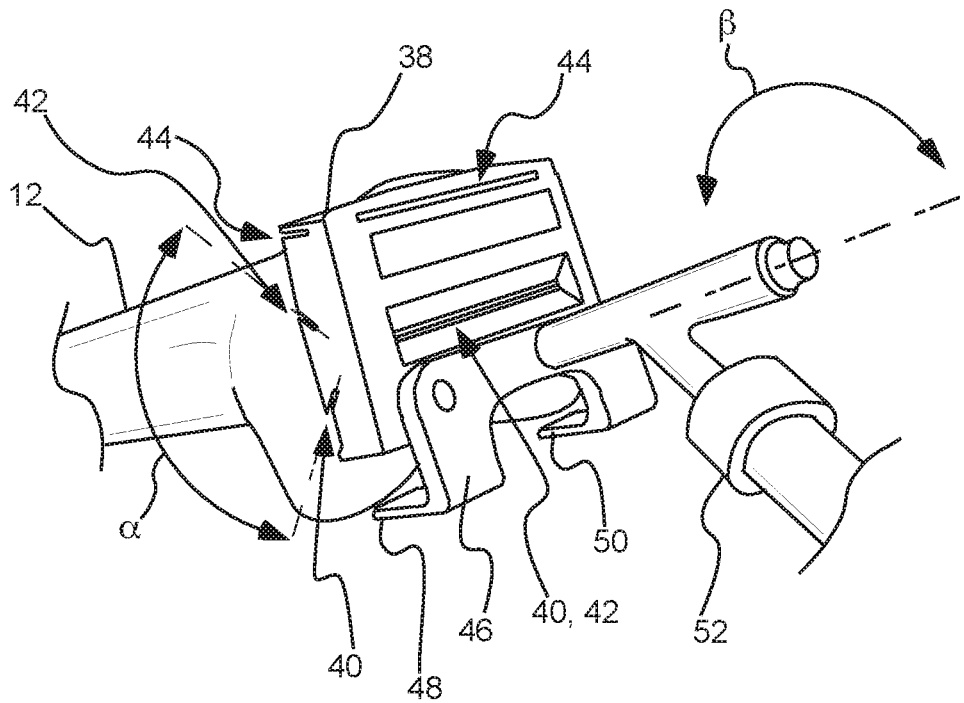
FIG. 5 is a perspective view the femur of FIG. 1 with an A/P chamfer cutting block positioned thereon.

Turning to FIG. 5, in one aspect of the invention an A/P chamfer cutting block 38 can be provided. The A/P chamfer cutting block can be aligned on and fixed to the axial cut surface 14 in a number of manners known to those of ordinary skill in the art. The A/P chamfer cutting block can include one or more saw blade slots or guides 40, 42, etc. The saw blade slots can be operable to receive the saw blade to aid in forming chamfer or condyle cuts in the femur to shape the femur to receive the implant component. The chamfer saw blade slots can be angled relative to one another at angle shown of "a". The angle α can vary, depending upon the implant system being used, but is generally between about 0 degrees and about 180 degrees.

In the embodiment shown, the A/P chamfer cutting block 38 can include or can carry at least one rotational guide 46. The rotational guide can include a pair of alignment feet or tabs 48, 50. These tabs can be placed on the posterior surface of at least one of the medial condyle or the lateral condyle to thereby rotationally orient the A/P chamfer cutting block relative to the femur. The rotational guide can be used when the implant must be adjusted (or rotated) based on the patient's anatomy. That is, the rotational guide can be used to appropriately externally rotate the femoral component for optimal biomechanics, as per surgical standard method, when it must be adjusted (or rotated) based on the patient's anatomy. A handle 52 can be fixed to the rotational guide to aid in positioning the rotational guide (and hence the A/P chamfer cutting block) to the femur.

Utilizing the present technology, a surgeon or technician can relatively easily determine the proper rotation and the alignment feet or tabs 48, 50 can be attached to the rotational guide 46 at fixed rotations. Once the known rotation is determined, a technician or the surgeon can fix the rotational guide to the chamfer cutting block to achieve this rotation. While these fixed rotations can vary, in one embodiment, they are selected from either a 3 degree rotation or a 5 degree rotation. The chamfer cutting block can then be properly aligned on the axial cut surface prior to forming any chamfer or condyle cuts.

In addition to the structural components described above, the present technology also provides methods of determining the proper size of a femoral implant component, methods of preparing a distal end of a femur for implantation. In one particular example, the technology provides a method of determining a size of a femoral component to be implanted in a patient. In this example, a distal cutting block can be positioned on a distal end of a patient's femur, the distal cutting block having a first saw blade slot associated therewith. A saw blade can be positioned in the first saw blade slot to form an axial cut surface on the distal end of the patient's femur, at least a portion of the axial cut surface extending through the medial condyle. A maximum distance of the axial cut surface across the medial condyle can measured. A femoral component can be selected based on the maximum distance measured. In one example, the femoral component can be selected based solely on the maximum distance measured.

Measuring the maximum distance can include measuring using nominal sizing indicia carried by the saw blade used to form the axial cut surface. The nominal sizing indicia carried by the saw blade can increment negatively from an anterior top of concavity of the medial condyle to a posterior top of concavity of the medial condyle, when the saw blade is positioned on the axial cut surface of the patient's femur. The nominal sizing indicia can be carried by the saw blade and can include incremental indicia correlating to nominal femoral components. Measuring the maximum distance can include measuring using an image of the axial cut surface.

Selecting a femoral component can include comparing the maximum distance measured to a set of femoral implants having varying nominal sizes. The method can include positioning an A/P chamfer cutting block on the axial cut surface, the A/P chamfer cutting block carrying at least one rotational guide, and positioning the at least one rotational guide on a posterior surface of at least one of the medial condyle or the lateral condyle to thereby rotationally orient the A/P chamfer cutting block. The one or more rotational guides can be attached to the A/P chamfer cutting block at a fixed orientation based on the axial cut surface.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

I claim:

1. A system for preparing a femur to receive an implant, comprising:
    a saw blade, positionable in a first saw blade slot of a distal cutting block and operable to form an axial cut surface on the patient's femur, the saw blade carrying nominal sizing indicia that increments negatively from an anterior top of concavity of the medial condyle to a posterior top of concavity of the medial condyle, when the saw blade is positioned on the axial cut surface of the patient's femur; and
    an A/P chamfer cutting block positionable on an axial cut surface of a femur, the A/P chamfer cutting block carrying at least one rotational guide, the at least one rotational guide positionable on a posterior surface of at least one of the medial condyle or the lateral condyle of the patient's femur to thereby rotationally orient the A/P chamfer cutting block relative to the patient's femur.

2. The system of claim 1, wherein the nominal sizing indicia carried by the saw blade includes incremental indicia correlating to nominal sizes of femoral components.

3. The system of claim 1, wherein the nominal sizing indicia is carried on a first side of the saw blade, and further comprising physical dimensional indicia carried by a second side of the saw blade, the physical dimensional indicia correlating to a physical width of femoral components.

4. The system of claim 1, wherein the A/P chamfer cutting block includes second and third saw blade slots, the second and third saw blade slots being angled relative to one another at an angle between 0 degrees and 180 degrees.

5. A system for preparing a femur to receive an implant, comprising:
    a distal cutting block, operable to be positioned on a distal end of the femur, the distal cutting block including a first saw blade slot associated therewith;
    a saw blade, positionable in the first saw blade slot and operable to resect the femur to form an axial cut surface thereon, the first saw blade carrying nominal sizing indicia; and
    an A/P chamfer cutting block, the A/P chamfer cutting block including at least a second saw blade slot associated therewith and carrying at least one rotational guide, the at least one rotational guide operable to rotationally orient the A/P chamfer cutting block relative to the femur.

6. The system of claim 5, wherein the nominal sizing indicia carried by the saw blade increments negatively from an anterior top of concavity of the medial condyle to a posterior top of concavity of the medial condyle, when the saw blade is positioned on the axial cut surface of the patient's femur.

7. The system of claim 5, wherein the nominal sizing indicia is carried on a first side of the saw blade, and further comprising physical dimensional indicia carried by a second side of the saw blade, the physical dimensional indicia correlating to a physical width of femoral components.

8. The system of claim 5, wherein the at least one rotational guide is removably attached to the A/P chamfer cutting block.

9. A system for preparing a femur to receive an implant, comprising:
    a saw blade, positionable in a first saw blade slot of a distal cutting block and having one or more cutting teeth formed on a distal end thereof, the cutting teeth of the saw blade being operable to form an axial cut surface on the patient's femur;
    the saw blade carrying sizing indicia that increments negatively from an anterior top of concavity of the medial condyle to a posterior top of concavity of the medial condyle, when the saw blade is positioned on the axial cut surface of the patient's femur, the sizing indicia carried by the saw blade including incremental indicia correlating to nominal sizes of femoral components; and
    an A/P chamfer cutting block positionable on an axial cut surface of a femur, the A/P chamfer cutting block carrying at least one rotational guide, the at least one rotational guide positionable on a posterior surface of at least one of the medial condyle or the lateral condyle of the patient's femur to thereby rotationally orient the A/P chamfer cutting block relative to the patient's femur.

10. The system of claim 9, wherein the nominal sizing indicia is carried on a first side of the saw blade, and further comprising secondary indicia carried by a second side of the saw blade.

11. The system of claim 9, wherein the at least one rotational guide is removably attached to the A/P chamfer cutting block.

\* \* \* \* \*